US006230052B1

(12) United States Patent
Wolff et al.

(10) Patent No.: US 6,230,052 B1
(45) Date of Patent: May 8, 2001

(54) DEVICE AND METHOD FOR STIMULATING SALIVATION

(75) Inventors: Andy Wolff, Hatamar, 60917, Harutzim; Azgad Yellin, Kfar Saba, both of (IL)

(73) Assignee: Andy Wolff, Harutzim (IL)

( * ) Notice: Subject to any disclaimer, the term of this patent is extended or adjusted under 35 U.S.C. 154(b) by 0 days.

(21) Appl. No.: 09/239,314

(22) Filed: Jan. 29, 1999

(51) Int. Cl.$^7$ ................ A61N 1/20; A61N 1/05
(52) U.S. Cl. ............... 607/2; 607/116; 607/72; 607/134
(58) Field of Search ................ 607/2, 48, 72, 607/116, 119, 134, 149

(56) References Cited

U.S. PATENT DOCUMENTS

| | | | |
|---|---|---|---|
| 3,259,129 | * | 7/1966 | Tepper ........................ 607/134 |
| 4,244,373 | | 1/1981 | Nachman . |
| 4,519,400 | | 5/1985 | Brenman et al. . |
| 4,637,405 | | 1/1987 | Brenman et al. . |
| 5,188,104 | | 2/1993 | Wernicke et al. . |
| 5,199,430 | | 4/1993 | Fang et al. . |
| 5,370,670 | | 12/1994 | Chancellor . |
| 5,591,216 | | 1/1997 | Testerman et al. . |
| 5,725,564 | * | 3/1998 | Freed et al. . |

FOREIGN PATENT DOCUMENTS

| | | | |
|---|---|---|---|
| 278847 | * | 8/1988 | (EP) ........................ 607/134 |
| 090001594B | * | 2/1992 | (NL) ........................ 607/116 |

OTHER PUBLICATIONS

Albrekisson et al, "State of the Art in Oral Implants", *J. Clin. Periodontol.*, 18:474–481, 1991.

Chou et al, "Electrical Stimulation of Salivary Flow in Patients with Sjögren's Syndrome", *J. Dent. Res.*, 67(10): 1334–1337, 1988.

Weiss, Jr., et al, "Use of an Electronic Stimulator for the Treatment of Dry Mouth", *J. Oral Maxillofac. Surg.*, 44:845–850, 1986.

Implanet.com: Literature and book reviews: Osseointegration, 1997.

Sreebny et al, "A Reference Guide to Drugs and Dry Mouth–2nd Ed.", *Gerodontology*, 14(1):33–47, 1997.

"Handbook of Autonomic Nervous System Dusfunction", A. D. Korczyn, Ed., Marcel Dekker, N.Y., Chap 19, pp 293–309.

* cited by examiner

*Primary Examiner*—Carl H. Layno

(57) ABSTRACT

An implantable device for inducing salivation by neural stimulation at neurally sensitive location within an oral or perioral tissue of a user. The device includes a housing adapted to be permanently implanted within the oral or perioral tissue. The housing has an enclosure therein for engaging an electrical signal generator. The signal generator includes a power source and at least one electrode operatively associated with the housing and electrically coupled to the signal generator. The electrode is so positioned with respect to the housing so as to form an electrical contact with the oral or perioral tissue and in operative contact with a neurally sensitive location of the oral or perioral tissue, the stimulation of which by electrical energy can induce salivation when the housing is operatively disposed, whereby the electrode applies a signal generated by the signal generator to the sensitive location of the oral or perioral tissue to induce salivation.

13 Claims, 1 Drawing Sheet

DEVICE AND METHOD FOR STIMULATING SALIVATION

FIELD AND BACKGROUND OF THE INVENTION

The present invention relates to a device and method for stimulating salivation, and more particularly, to an implantable device and a method of using same for stimulating salivation by the application of electrical energy to nerves in the region of the oral cavity to produce salivation by reflex action, by creating parasympathetic outflow to the salivary glands, parotid, submandibular or sublingual.

The following background information is derived, in part, from A. D. Korczyn, Ed. "Handbook of autonomic nervous system dysfunction" Marcel Dekker, N.Y., 1995, pp. 293–309.

Salivary glands have been recognized since the $19^{th}$ century as typical effector organs of the autonomic nervous system. The classic experiments of Pavlov are a good example of the interest that salivary glands have stirred up among scientists. They illustrate the decisive control the autonomic nervous system exerts on salivary gland. Therefore, salivary glands are sensitive markers of autonomic nervous system function and, as such, may present a variety of disorders related to autonomic nervous system dysfunction.

Applied Anatomy of the Salivary Glands: Human beings possess three pairs of major salivary glands—parotid, submandibular, and sublingual—and a myriad of minor salivary glands spread throughout the oral mucosa. All salivary glands share a common parenchymal structure of acinar units and ducts. The former are composed of acinar cells encircled by myoepithelial cells and circumscribing the acinar lumen. The acinar lumen drains into the ductal system, which reaches the oral cavity. The salivary gland stroma is made up of neurovascular structures and scarce connective tissue.

The salivary gland morphology will be described succinctly here. The parotid glands, the largest of the salivary glands, lie underneath the skin of the cheeks. They secrete their saliva via Stensen's ducts, which open into the oral cavity opposite the upper second molars. Parotid glands have predominantly serous acini, and therefore the fluid they secrete is "watery" and not viscous, as is the fluid secreted by mucous glands.

Innervation of the parotid glands is provided by parasympathetic and sympathetic fibers. The preganglionic parasympathetic fibers of the parotid glands arise from the inferior salivary nucleus in the medulla, from where they travel through the glossopharyngeal nerve, the tympanic nerve and plexus, and the lesser petrosal nerve into the otic ganglion. Here they synapse with fibers in the auriculotemporal nerve, reaching the parotid gland. The sympathetic innervation originates in the superior cervical ganglion, and contacts the parotid gland via the plexus of the external carotid.

The submandibular glands are the second largest salivary glands. These glands and the sublingual glands are situated at the floor of the mouth. These glands empty their secretions into the oral cavity through ducts whose foramina are located sublingually. While submandibular glands have a mixed structure of serous and mucous secretory units, sublingual glands are mainly mucous.

The innervation of submandibular and sublingual glands is similar. Preganglionic parasympathetic innervation originates from the superior salivary nucleus in the pons, reaching the submandibular ganglion after passing along the nervus intermedius (facial nerve) and the chorda tympani. The sympathetic innervation arises from the superior cervical ganglion and reaches the glands by way of the facial artery plexus.

Secretion of Saliva: The greatest part of saliva is secreted by the parotid and submandibular glands. Other contributions to saliva include sublingual and minor gland secretions, gingival exudate, desquamated epithelial cells, blood cells, microorganisms, and their products.

Saliva performs a crucial role in the oral cavity. The full accomplishment of salivary functions depends on proper salivary flow rate and composition. Taste perception is facilitated by saliva carrying food particles onto the taste buds in an appropriate dilution. Salivary amylase and lipase start the digestion of starch and fat. Saliva is also important in the formation of the food bolus and the salivary lubricatory glycoproteins permanently coat oral surfaces, assisting in food mobility and reducing friction between the different oral structures (teeth, tongue, cheeks, lips) and between the structures and foreign elements (food, dental prostheses).

Salivary lubrication, repair, lavage, antimicrobial, and buffering properties contribute significantly to the maintenance of oral hard and soft tissue integrity.

The secretion of saliva is regulated by the autonomic nervous system, with a minor role played by hormones and autocoids. Salivary secretion fluctuates between minimal and maximal rates. The basal secretion of saliva, which is due to the spontaneous activity of the salivary nuclei, displays a circadian rhythm of high amplitude.

The stimuli that enhance salivation are related to eating: tasting, smelling or seeing food, and chewing. These peripheral stimuli are transmitted to the central nervous system, exciting efferent salivary fibers. During meals saliva production rises 5–50 fold over basal secretion.

The accumulated knowledge on salivary gland physiology, which is mostly based on studies performed on animals, explains the role of the autonomic nervous system in saliva secretion. The two autonomic divisions act synergistically to produce salivation by the salivary glands, although sublingual and labial salivary glands lack sympathetic control.

In the parotid and submandibular glands the parasympathetic system is mostly responsible for the water and electrolyte secretion, whereas the sympathetic system mainly regulates the protein (e.g., amylase) secretion.

Autonomic Effects on Acinar Secretory Cells: Postganglionic sympathetic fibers release norepinephrine, which activates alpha- and beta-adrenergic receptors on salivary glands. The parasympathetic fibers release acetylcholine, vasoactive intestinal peptide (VIP), and substance P. Beta-adrenergic and muscarinic cholinergic receptors are present at a much higher density on parotid membranes than other receptors.

The signal transduction mechanisms differ among the salivary gland receptors. Beta-adrenergic and VIP receptors activate adenylate cyclase that catalyzes cAMP formation from ATP. Conversely, alpha-2-adrenergic receptor activation blocks cAMP generation and inhibits salivary secretion. Muscarinic cholinergic, alpha-1-adrenergic, and substance P receptors activate phospholipase C, and, as a result, diacylglycerol (DAG) and inositol triphosphate (ITP) are formed from the hydrolysis of phosphatidylinositol-4,5-biphosphate.

Each second messenger created by the transduction mechanisms mobilizes its own pathway. Signaling of cAMP leads primarily to exocrine protein secretion. DAG likewise induces protein excretion, but to a much lower extent. The pathway of ITP involves calcium mobilization, which causes fluid secretion through the activation of ion channels. Unlike the pancreas and the kidney, fluid production by salivary gland does not depend upon perfusion pressure but on the creation of osmotic pressure by active ion transport across the acinar cells into the lumen. This osmotic pressure drags water from the interstitium into the acinar lumen to produce an isotonic fluid, termed promary saliva.

Autonomic Effects on other Salivary Gland Components: Myoepithelial cell contraction, which contributes significantly to saliva secretion, is induced by parasympathetic and sympathetic stimulation, acting upon muscarinic cholinergic and alpha-adrenergic receptors, respectively.

Primary saliva fluid, secreted from acinar cells, is modified in the ductal system to produce a hypotonic fluid, which is secreted into the oral cavity. Sodium and chloride are reabsorbed into ductal epithelial cells, which, in turn, release potassium and bicarbonate ions. A short contact time of primary saliva with ductal cells, which occurs when salivary flow increases upon salivary gland stimulation, diminishes electrolyte interchange. The ductal electrolyte transport is under autonomic control, but, in addition, it is influenced also by hormonal and metabolic factors.

Contraction of glandular blood vessels is the only sympathetic inhibitory effect of salivary gland function. This particular activity takes place independently of other sympathetic regulatory influences on the salivary gland. Parasympathetic-induced vasodilatation is mediated by both cholinergic and VIP receptors. When vasodilatation is needed in order to supply water for saliva production, parasympathetic influences largely overpower sympathetic vasoconstrictive effects.

Dysfunction of Salivary Glands: Autonomic nervous system abnormalities are mostly manifested by salivary gland hypofunction (SGH). Sialorrhea (excessive drooling) and hypersalivation are controversial terms that have been traditionally described in a number of conditions such as cerebral palsy, Parkinson's disease and seasickness. However, the scientific literature on salivary gland function in these disorders has shown either a normal or decreased salivary output or lacks adequate quantitative salivary measurements.

Xerostomia (sensation of dry mouth) may be due to a variety of factors, although SGH is its most frequent cause. SGH generates xerostomia when salivary flow does not suffice to compensate for loss of fluid from the mouth. Oral fluid is consumed by swallowing, absorption by the oral mucosa, and evaporation from the mouth. Xerostomia is thought to become a significant symptom when the unstimulated flow is reduced by 50% or more.

Xerostomia is a common symptom and may affect between one-fifth and one-third of the adult population. It affects women more commonly than men. When caused by SGH, xerostomia may be accompanied by a variety of oral hard and soft tissue changes. The lower the salivary flow rate, the less salivary defense and lubrication components enter the oral cavity. The mucosal tissues may become painful, "burning", ulcerated, or atrophic. An increased rate of dental caries with a distinctive cervical pattern of decay, which is extremely difficult to treat, is typically seen. Xerostomic denture wearers exhibit a high prevalence of oral candidiasis.

Decreased salivary secretion may lead to functional oral disturbances as well. Chewing, swallowing, and speaking are difficult and taste sensation may be diminished. These disorders compromise not only the biological integrity of the individual but also the general quality of life and well-being.

SGH can be linked primarily to autonomic nervous system dysfunction or to salivary gland parenchyma changes. The most prominent of the former is caused by the use of pharmacological agents, while Sjogren's syndrome is the most common condition leading to significant salivary gland structural alterations.

Causes of xerostomia in cases of normal salivary gland function include body dehydration, oral mucosal sensory alterations, psychological disturbances and habits, such as smoking, mouth breathing and alcohol consumption. Causes of xerostomia in cases of salivary gland hypofunction primarily associated with autonomic nervous system disorders include intake of drugs acting on the autonomic nervous system, and poisoning, Alzheimer's disease, depression, diabetes, Fabry's disease, salivary gland denervation and pure dysautonomias. Causes of xerostomia in cases of salivary gland hypofunction primarily associated with salivary gland parenchymal alterations include Sjogren's syndrome, head and neck radiotherapy, bone marrow transplantation, chronic hepatitis C, HIV infection, sarcoidosis, amyloidosis and hyperlipoproteinemia.

The question of whether age, per se, is a causative factor of SGH has not been completely determined. The reports in the literature on the impact of aging on salivary flow are conflicting. The clinician should be cautious in considering advanced age, per se, as the reason for complaints of xerostomia among aging patients. Intake of drugs or coextistent disease, so common in old age, are co-founding that could also explain these symptoms.

SGH Induced by Drugs and Poisoning: The use of medication is the most common cause of SGH. A high percentage of dental patients aged 65 and above (73%) were found to take prescription drugs routinely. A majority of them (87%) take multiple medications. Approximately half of the institutionalized geriatric population has been reported to receive one or more drugs with a hyposalivatory side effect.

A list of over 400 drugs that cause xerostemia as an adverse side effect has been published (Sreebny L M and Schwartz S S. A reference guide to drugs and dry mouth. $2^{nd}$ edition, Gerodonotology 1997; 14:33–47, which is incorporated by reference as if fully set forth herein). Salivary flow is particularly reduced when two or more hyposalivatory drugs are taken simultaneously. The use of medications with xerostomic effects has been found to be a good predictor of root caries in the elderly.

Drugs can affect autonomic nervous system function at several sites: central nervous system (CNS) centers: preganglionic, ganglionic, postganglionic, and effector site neurotransmission; and effector cells. The classes of pharmacological agents causing xerostomia include (i) agents affecting primarily the autonomic nervous system; (ii) agents with anticholinergic side effects; and (iii) agents causing xerostomia by other or unknown mechanisms. Agents affecting primarily the autonomic nervous system include peripheral alpha adrenergic blocking agents, e.g., prazosin, doxazosin, terazosin and alfuzosin; beta-blocking agents, e.g., propranolol, atenolol, esmolol, metoprolol and oxprenolol; antimuscarinic agents, e.g., atropine, scopolamine, propantheline, pirenzepine and trihexyphenidyl; central alpha-2 agonists, e.g., clonidine and methlydopa; neuron-blocking agents, e.g., bretylium and monoamine oxidase inhibitors; and ganglion-blocking agents, e.g., mecamylamine. Agents with anticholinergic side effects include dopamine receptor-blocking agents, e.g., phenothiazines (i.e., fluphenazine, thioproperazine, levomepromazine and thioridazine) and thioxanthenes; tricyclic antidepressants, e.g., amitriptyline, clomipramine, desipramine, doxepin and imipramine; benzodiazepines, e.g., clonazepam, clorazepate and diazepam; H1 antihistamines; Lithium salts; and other drugs, such as, disopyramide and anorexiants. Agents causing xerostomia by other or unknown mechanisms include calcium channel blockers, e.g., verapamil (alpha-blocking activity); diuretics; narcotic analgesics; steroids; nonsteroidal anti-inflammatory drugs; angiotansin converting enzyme inhibitors and serotonin specific receptor inhibitors.

Most of the literature on this issue is based on patients' subjective complains and basic research. Reports on quantitative salivary flow data obtained through well-controlled clinical studies on subjects receiving medication are scarce.

Dry mouth is a clinical manifestation of botulism and poisoning with atropine and scopolamine. Botulinum toxins interfere with acetylcholine release from cholinergic nerve endings. Atropine produces muscarinic receptor blockage.

Salivary Gland Disorders Induced by Diseases:

Alzheimer's Disease: It has been reported that submandibular gland function is compromised, (while parotid function is unaltered), among nonmedicated patients with Alzheimer'S disease, possibly due to dehydration and structural abnormalities of the pons.

Depression: Stress-related dry mouth is the result of central inhibition on the salivary centers. Whole and parotid salivary flow rates have been found to be reduced among depressed patients, particularly in involutional and manic-depressive cases. However, since most depressed individuals are taking medication, it is now difficult to perform salivary studies on these patients.

Diabetes: Thirst is a frequent complaint of diabetic patients. However, the literature is controversial as to the relationship among thirst, xerostomia, and SGH among diabetic patients. In one study, parotid function has been found to be reduced in diabetic patients with peripheral neuropathy, but normal in other patients with diabetes. These results are consistent with parasympathetic denervation of the parotid gland in diabetic autonomic neuropathy. However, in other studies diabetic autonomic neuropathy was associated with either no change in whole salivary flow rate or even an increase in parotid gland output.

Fabry's Disease: Fabry's disease is a metabolic disorder accompanied by sympathetic and parasympathetic involvement. Reduced saliva production is one of the autonomic manifestations of this disease.

Salivary Gland Denervation: After division of autonomic fibers, neurotransmitters are released in greater amounts until stores become depleted. This induces a degenerative secretion, lasting a few days. The acinar cells gradually develop supersensitivity to neurotransmitter stimulation. At later stages after parotid denervation, a paradoxical phenomenon has been described: copious salivation following atropine administration, similar to the paradoxical effect of atropine on the denervated pupil.

Pure Dysautonomias: Cholinergic dysfunction leading to SGH has been described in Shy-Drager syndrome, postganglionic cholinergic dysautonomia, and panautonomic dysfunction. Familial dysautonomia, also known as Riley-Day syndrome, is an autosomal recessive disease occurring almost exclusively in Jewish children of Askenazi origin. This disease is characterized by progressive impairment of sensory and autonomic functions. One of the many signs reported in this disorder is drooling, either due to "denervation supersensitivity" of the partially denervated salivary gland, resulting in hypersalivation, or impaired deglutition.

Sialadenosis: Sialadenosis is a symmetrical, painless, noninflammatory, recurrent parotid swelling, associated with a variety of metabolic alterations, such as diabetes mellitus, liver diseases, malnutrition and the use of antihypertensive agents. The swelling of the parotid glands is the manifestation of acinar cell enlargement in response to increased sympathetic activity. In fact, considerably higher beta-receptor concentration in salivary gland were found in sialadenosis. Adequate evidence of the presence of alterations in salivary secretion rate is lacking.

Bell's Palsy: The differential assessment of bilateral submandibular gland function as part of chorda tympani function appears to be valuable in the prediction of Bell's Palsy prognosis. This assessment can be carried out by means of submandibular duct cannulation or scintigraphy. If the affected side exhibits reduction of at least 75% compared to the normal side, there is usually no recovery. An increased salivary concentration of $Na^+$ has been found in patients with facial paralysis, possibly due to alterations in the ductal $Na^+$ pump.

Treatment of Autonomic Nervous System-Associated Salivary Gland Dysfunction: It is crucial to instruct patients with dry mouth on the importance of maintaining oral health. A well-designed preventive program should include meticulous oral hygiene procedures and the routine use of fluoride supplements.

Modification of Drug Regimen: Patients often continue to take medications even after the original cause that has led to their prescription has been eliminated. In such cases, it might be possible to suspend or reduce the intake of the offending drugs. When this is not possible, splitting of the daily dose into smaller, more frequently taken doses may alleviate the xerostomic effects. Drug scheduling may be modified to achieve peak blood levels that do not coincide with periods during the day when maximal oral dryness is reported by the patient. In other cases, substitution of drugs with equipotent agents with fewer side effects may be attempted. Yet, in many cases no substitute is available, and xerostomia persists.

Salivary Gland Chemical Stimulation: Chemical stimulation of salivary glands, may have good symptomatic benefit on patients with dry mouth, providing the oral cavity with its natural saliva. The flow of saliva through the salivary gland ducts also helps to prevent ascending infections of the salivary glands. However, only patients with responsive salivary gland tissue may benefit from this approach. Usually chewing gums formulated with noncariogenic sweeteners and flavors are better accepted by patients with dry mouth than are mouthwashes acting as salivary stimulants and substitutes. The salivary gland-stimulating effect of citric acid is short acting and, therefore, frequently not satisfactory to achieve symptomatic improvement of xerostomia. The effectiveness of citric acid is also limited by its irritating effects on the oral mucosa. Patients should be cautioned about the demineralizing effect on the teeth of frequent use of citric acid rinses.

Saliva Substitutes: Treatment of SGH base on artificial saliva is largely palliative. It attempts, by the use of a variety of oral rinses, to provide lubrication of the oral soft tissues and to limit damage to the hard tissues. However, treatment of the sensation of dryness and soft tissue changes with saliva substitutes is often unsuccessful.

Carboxymethycellulose (CMC) and animal mucins are used to replace the salivary effects (lubrication, viscosity) on oral functions, such as food emulsion and swallowing. However, a study has shown that one-third of patients with dry mouth have found CMC-based oral rinses inadequate to treat their condition.

Other components of artificial salivas are sweeteners (xylitol or sorbitol) and electrolytes. The addition of electrolytes is aimed at mimicking natural saliva composition and at providing the potential for remineralization.

Systemic/Local Sialogogues: Pilocarpine produces its cholinomimetic effects chiefly by a direct action on the autonomic effector cells, although ganglionic stimulation may participate in the production of its total pattern of response. Administration of 5 mg pilocarpine HCl has been shown to increase the output of parotid and submandibular secretions and to relieve xerostomia for up to 3 hours.

A major drawback of pilocarpine is its potential for inducing adverse cholinergic effects on patients with cardiovascular alterations, asthma, or active duodenal ulcers. However, no alterations in basic cardiovascular parameters were observed in patients with dry mouth who have received 15–20 mg pilocarpine daily. Mild side effects, such as sweating, flushing, and urinary urgency were occasionally observed.

The muscarinic cholinergic stimulating agent bethanecol chloride and the cholinesterase inhibitor pyridostigmine have been used to treat xerostomia induced by a variety of factors. Subjective improvement of xerostomia as a result of anetholetrithione intake has been reported. It is believed that the mechanism of action of anetholetrithione on salivary glands is linked to proliferation of muscarinic receptors on the acinar cell membranes. Since a major part of the drug is metabolized in the liver, its use is contraindicated in patients with significant hepatic diseases.

It has recently been reported that yohimbine induces a significant increase in saliva secretion in healthy subjects and in depressed patients treated with tricyclic antidepressants. Yohimbine enhances norepinephrine release from nerve terminals by preferential blockade of presynaptic alpha-2 receptors: it acts possibly also in chorda tympani nerve endings leading to enhanced acetylcholine release and submandibular saliva secretion. However, high doses of the drug may produce significant autonomic effects, such as increases in systolic blood pressure and anxiety. Another drawback of yohimbine may be the highly variable bioavailability of the drug in humans.

The mucolytic agent bromhexine has been used to treat xerostomia in patients with Sjogren's syndrome, but no conclusive evidence on the utility of this agent is available.

Slow-releasing devices to be attached to or placed around teeth or implanted into the gum are disclosed, for example, in U.S. Pat. Nos. 3,624,909; 3,688,406; 4,020,558; 4,175,326; 4,681,544, 4,685,883, 4,837,030; 4,919,939; 5,614,223 and 5,686,094. These devices serve for releasing various medicaments within the oral cavity of a patient. The latter two patents disclose devices for controlably releasing drugs for the treatment of xerostomia.

Electric Stimulation: U.S. Pat. Nos. 4,519,400 and 4,637,405 teach a stimulator for inducing salivation by neural stimulation. The stimulator includes a housing which may be received in the oral cavity of a user, the housing enclosing electronic signal generating means and electrodes for applying a signal to neurally sensitive locations of the oral cavity to induce salivation. In its method aspect, the invention involves stimulation of salivation by the application of an electrical signal to neurally sensitive locations.

This device has numerous limitations. In one embodiment thereof, it is held in the mouth cavity of a user for a time period and then it is removed therefrom, to be reinserted into the mouth cavity at a later time. In another version, it is held in place by being connected to a tooth of the upper jaw. This configuration is limiting because it causes great discomfort to the user and affects the user's ability to speak, eat and/or drink.

There is thus a widely recognized need for, and it would be highly advantageous to have, an implantable device and a method of using same for stimulating salivation, devoid of the above limitations.

SUMMARY OF THE INVENTION

According to one aspect of the present invention there is provided an implantable device for inducing salivation by neural stimulation at neurally sensitive locations within an oral or perioral tissue of a user, comprising a housing adapted to be permanently implanted within the oral or perioral tissue, the housing having an enclosure therein, an electrical signal generator disposed in the enclosure, the signal generator including a power source, at least one electrode operatively associated with the housing and electrically coupled to the signal generator, the electrode being so positioned with respect to the housing so as to form an electrical contact with the oral or perioral tissue and in operative contact with a neurally sensitive location of the oral or perioral tissue, the stimulation of which by electrical energy can induce salivation when the housing is operatively disposed, whereby the electrode applies a signal generated by the signal generator to the sensitive location of the oral or perioral tissue to induce salivation.

According to another aspect of the present invention there is provided a method for stimulating salivation, the method comprising the steps of (a) forming at least one cavity in an oral or perioral tissue; (b) providing at least one implantable device for inducing salivation, including a housing adapted to be permanently implanted within the cavity, the housing having an enclosure therein, an electrical signal generator disposed in the enclosure, the signal generator including a power source, at least one electrode operatively associated with the housing and electrically coupled to the signal generator, the electrode being so positioned with respect to the housing so as to form an electrical contact with the oral or perioral tissue and in operative contact with a neurally sensitive location of the oral or perioral tissue, the stimulation of which by electrical energy can induce salivation when the housing is operatively disposed, whereby the electrode applies a signal generated by the signal generator to the sensitive location of the oral or perioral tissue to induce salivation; and (c) implanting the at least one implantable device in the at least one cavity.

According to further features in preferred embodiments of the invention described below, the implantable device further comprising a switch element associated with the housing and the signal generator for activating and deactivating the signal generator.

According to still further features in the described preferred embodiments the switch element is adapted to protrude from within the oral or perioral tissue into the oral cavity, so as to be operable by the user or the dentist.

According to still further features in the described preferred embodiments the switch element includes a potentiometer for controlling a parameter of the signal generated by the signal generator.

According to still further features in the described preferred embodiments the switch is remote controlled.

According to still further features in the described preferred embodiments the implantable device further comprising at least one anchoring element connected to the housing, the at least one anchoring element serves for anchoring the device within the oral or perioral tissue.

According to still further features in the described preferred embodiments the housing includes a cover.

According to still further features in the described preferred embodiments the signal generator includes a mechanism for producing a series of pulses having an amplitude of about half to five volts, a pulse width of about 1–1000 micro-seconds and a frequency of about 10–160 Hz.

According to still further features in the described preferred embodiments the signal generator further includes a mechanism to turn the signal on and off at intervals of about one-half second.

According to still further features in the described preferred embodiments the signal generator further includes a multivibrator and a power amplifier.

According to still further features in the described preferred embodiments the method further comprising the steps of locating and stimulating the nerves of the oral or perioral tissue to identify locations which are sensitive to neural stimulation by electrical means prior to forming a cavity in an oral or perioral tissue, wherein the step of forming the cavity in the oral or perioral tissue is effected in these locations.

According to still further features in the described preferred embodiments the steps of locating and stimulating are performed by applying to the locations an electrical signal of a kind similar to the signal produced by the implantable device.

The present invention successfully addresses the shortcomings of the presently known configurations by providing a device for inducing salivation which is implanted within the oral or perioral tissue, to therefore eliminate the discomfort associated with using the prior art devices, which are placed in the mouth cavity.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
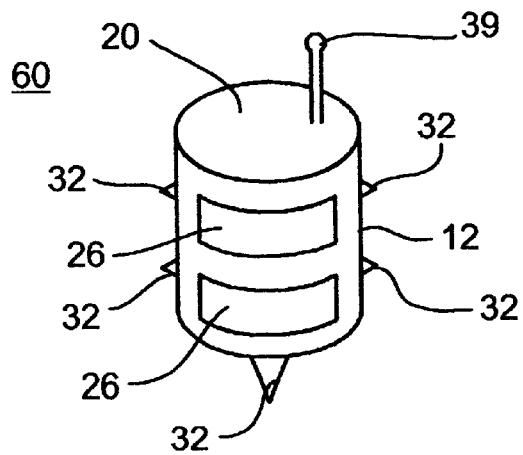
FIG. 1 is a simplified perspective view of an implantable device for stimulating salivation according to the present invention.

The present invention is of a device and method which can be used for stimulating salivation. Specifically, the present invention can be used for stimulating salivation in cases of chronic xerostomia. The main advantage of the present invention over the prior art is that the device according to the present invention is constructed and designed to be implanted within a tissue surrounding the mouth cavity, i.e., within oral or perioral tissue, e.g., within the gums, whereas the prior art teaches positioning the device in the mouth cavity against the palate, which causes great discomfort to the user.

The principles and operation of a device and method for stimulating salivation according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
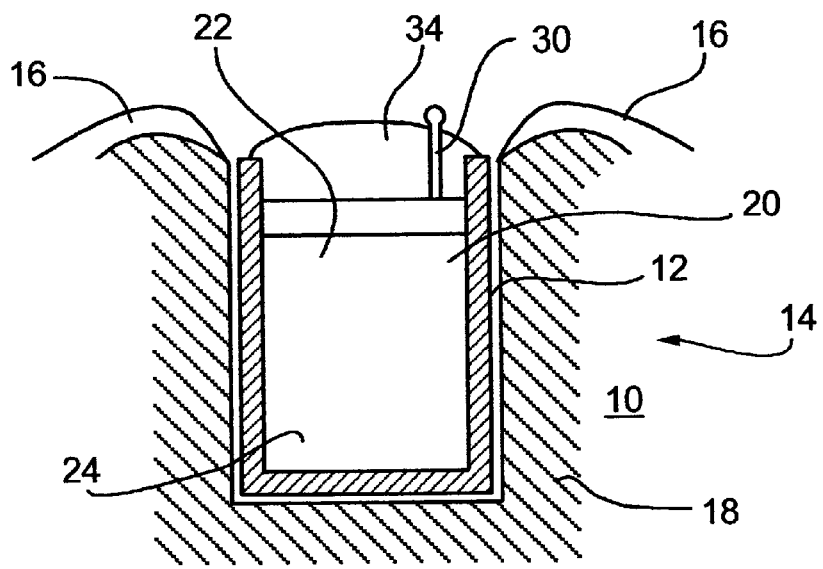
FIG. 2 is a simplified cross-sectional view of an implantable device for stimulating salivation according to the present invention.

Referring now to the drawings, FIGS. 1–2 illustrate the device for inducing salivation by neural stimulation at neurally sensitive locations within an oral or perioral tissue according to the present invention, which is referred to hereinbelow as implantable device 10.

As used herein in the specification and claims section below, the phrase "sensitive location" refers to any location, electrical stimulation thereof results in increased salivation.

As used herein in the specification and claims section below, the phrase "oral or perioral tissue" refers to any tissue surrounding the oral cavity and which is not more than 5 cm away from the surfaces defining the oral cavity, including both hard and soft tissues, such as, gums, jaw bones, palate and the like.

Implantable device 10 includes a housing 12. Housing 12 is adapted to be permanently implanted within the oral or perioral tissue of a user. As used herein in the specification and in the claims section that follows, the term "permanently" refers to a prolonged time period, e.g., several weeks to several months or preferably several years. To this end, housing 12 is preferably shaped as a capsule, sized to fit into a cavity 14, formed in the oral or perioral tissue of the user, which cavity 14 serves for accepting and anchoring device 10 therein. Exemplary cavity 14, shown in FIG. 2, is formed in a gum 16 and jaw bone 18 and is shaped to intimately accept device 10 therein. The dimensions of housing 12 are selected small enough to fit into cavity 14. Typically the height of housing 12 is between 1 and 25 mm, preferably, between 5 and 18 mm. Typically the diameter or width of housing 12 is between 1 and 50 mm, preferably, between 2 and 6 mm.

As used herein in the specification and in the claims section below, the terms "implant", "implanted" and "implantable" refer to a process of embedding device 10 in a dedicated cavity formed in an oral or perioral tissue, following which, device 10 may be either completely embedded in the tissue, so as to have no portion thereof protruding from the surface of the tissue, or alternatively, a portion of device 10 not greater than 40% of its volume, preferably not greater than 30% of its volume, more preferably not greater than 20% of its volume, most preferably not greater than 10% of its volume, protrudes from the surface of the tissue. Optimally, as shown in FIG. 2, device 10 is embedded in the tissue, so as to have no portions thereof actually protruding from the tissue, yet to enable access to device 10 so as to enable its simple removal from within the tissue, so as to enable, repair, total replacement and/or power source replacement.

Housing 12 is further designed to form an enclosure 20 therein. Enclosure 20 holds, within housing 12, an electrical signal generator 22 which includes a power source for supply of power, e.g., a battery 24, at least one electrode 26 (two are shown), operatively associated with housing 12 and electrically coupled to signal generator 22. Electrodes 26 are so positioned with respect to housing 12 so as to form an electrical contact with the walls of the cavity formed in the oral or perioral tissue and in operative contact with a neurally sensitive location of the oral or perioral tissue, the stimulation of which by electrical energy can induce salivation when housing 12 is operatively disposed, whereby electrodes 26 apply a signal generated by signal generator 22 to the sensitive location of the oral or perioral tissue to induce salivation. The moisture inherent to oral or perioral tissues and the intimate contact between housing 12 and therefore electrodes 26 which are positioned externally thereto, ensures good conductivity between electrodes 26 and the oral or perioral tissue to thereby effectively deliver the stimulating signal.

Figure 3:
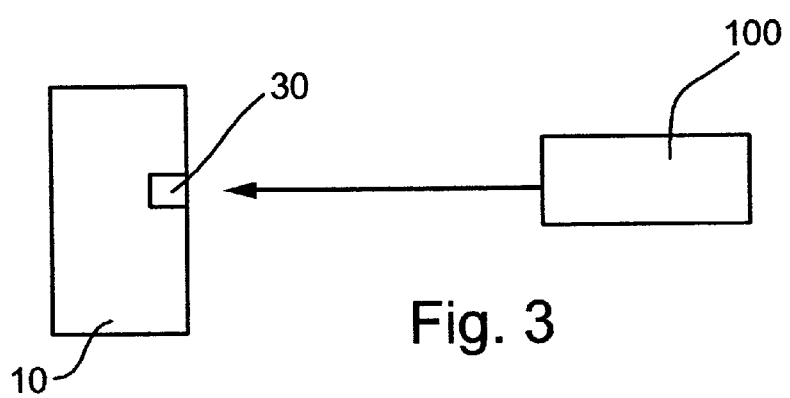
FIG. 3 is a schematic depiction of remote controlling and implantable device for stimulating salivation according to the present invention.

According to a preferred embodiment of the present invention implantable device 10 includes a switch element 30 associated with housing 12 and signal generator 22 for activating and deactivating signal generator 22. According to one embodiment of the present invention switch element 30 is adapted to protrude from within the oral or perioral tissue into the oral cavity, so as to be operable by the user or the dentist. Alternatively, as is shown in FIG. 3 switch element 30 forms an inner part of device 10 and is remote controlled by a remote control 100. In both cases, however, switch element 30 preferably includes a potentiometer for controlling a parameter of the signal generated by signal generator 22. Thus, a user can control both the operational state (on, off) and the level of operation of device 10 according to the needs changing in the course of day and night, etc.

According to a preferred embodiment of the present invention device 10 includes at least one anchoring element 32 connected to, or integrally formed with, housing 12. Anchoring element 32 can be, but it is not limited to, a spring element, a spike element, a thread element, a friction inducing element or a perforated structure for facilitated osseointegration, and serves for anchoring device 10 within cavity 14 formed in the oral or perioral tissue. Applications wherein anchoring elements 32 are retractable are envisaged. Such retractable anchoring elements 32 will facilitate the removal of device 10 from the oral or perioral tissue, when so required.

According to a preferred embodiment of the present invention device 10 includes a cover 34 for ensuring the integrity of the components thereof engaged within closure 20. Cover 34 can serve for power source 24 replacement without the need of removing device 10 from its position within the oral or perioral tissue.

One electronic circuitry by which stimulating signals can be produced according to the present invention is described in U.S. Pat. Nos. 4,519,400 and 4,637,405, which are incorporated herein by reference, and is therefore not further described herein in detail. Additional examples of circuits designed for application of electrical signals in a mouth of a patient are disclosed in U.S. Pat. Nos. 4,244,373 and 5,188,104, both are incorporated by reference as if fully set forth herein. It will be appreciated that other specific circuitry capable of performing the same function may occur to those skilled in the art. It should be understood that the electronic circuitry uses commercially available components, and because device 10 is intended for use within a cavity formed in oral or perioral tissue (making size an important consideration), the presently desired configuration of device 10 utilizes microminiature components in the "$SO_2$", "LIDS" or "DICE" size packages, although any standard CMOS equivalent integrated circuitry (chips) can be used to fabricate circuitry in even smaller dimensions.

The circuitry is preferably designed to produce an output of between 1 microA to 100 mA, preferably 10 microA to 50 mA, more preferably 1–25 mA, most preferably 8–16 mA, typically about 12 mA which is calculated on the basis of an assumed output voltage of about 4 volts into an impedance of about 330 ohms, and it will produce a constant output voltage regardless of the impedance fluctuations due to differential moisture level within the user's oral or perioral tissue. A current limited configuration, as is presently preferred, avoids high current spikes which might occur in low impedance conditions, and conserves battery power. In any case both DC and AC currents can be employed.

According to a preferred embodiment of the present invention signal generator 22 includes a mechanism for producing a series of pulses having an amplitude of about half to ten, preferably one to eight, more preferably two to seven volts, a pulse width of about 1–1000, preferably about 300–700, more preferably about 500 micro-seconds and a frequency of about 10–160, preferably about 20–100, more preferably, about 30–50 Hz. Preferably, signal generator 22 further includes a mechanism to turn the signal on and off at intervals of about one-half second. Further preferably, signal generator 22 further includes a multivibrator and a power amplifier.

As used herein in the specification and in the claims section below the term "about" means ±20%.

The following short description relates to the state-of-the-art oral implants. Oral implants have been used for a long time. There are soft tissue anchored oral implants, subperiosteal implants, single-crystal sapphire implants, Tubingen aluminum ceramic implants, transmandibular staple implants, Core-Vent titanium alloy implants, IMZ implants, ITI implants, Branemark implants, etc. Further details relating to each of which are disclosed in, for example, a paper by Albrektsson T and Sennerby L, entitled "State of the art in oral implants", J. Clin. Periodontol., 1991, Volume 18, pages 474–481, which is incorporated by reference as fully set forth herein. Any one of the above implants can be designed hollow to form housing 12 of device 10.

According to its method aspect, the present invention provides a method for stimulating salivation. The method according to the present invention is effected by implementing the following method steps, in which, in a first step, at least one cavity is formed in the oral or perioral tissue of a use. Then, device 10 as herein described is implanted in each of the cavities. Prior to the formation of cavities, the nerves of the oral or perioral tissue are located and stimulated to identify locations which are sensitive to neural stimulation by electrical means, whereas forming the cavities in the oral or perioral tissue is effected in these locations. Locating and stimulating the nerves are preferably performed by applying to the locations an electrical signal of a kind similar to the signal produced by implantable device 10 as herein described.

Several generations of device 10 according to the present invention can be envisaged. In a first generation a any given device 10 has constant electrical parameters. In a second generation of device 10 these constant electrical parameters are presetable by the dentist prior to implantation. In a third generation, device 10 has controllable or changeable electrical parameters which can be adjusted after implantation by the dentist. In a fourth generation, device 10 has controllable or changeable electrical parameters which can be adjusted by the user according to changing needs (e.g., eating as opposed to sleeping). In a fifth generation, changing the changeable electrical parameters is effected by remote control. In a sixth generation, changing the changeable electrical parameters is under the control of a salivation sensor which constantly senses mouth humidity and forms a feed-back loop with device 10. In a seventh generation, changing the changeable electrical parameters is under the control of the user's autonomic nervous and endocrine systems which form a feed-back loop with device 10.

The method and device according to the present invention can be used to treat cases of chronic xerostomia as described in the Background section above.

The advantage of the present invention over the prior art lies in its in tissue implantable design, which renders the use thereof substantially un-noticed by the user, resulting in higher compliance of usage, to thereby dramatically improve the health status of the patient. It will be appreciated in this respect that salivation, as achieved while implementing the present invention, is crucial for diminishing carries rate and fungal infection and for improving the speaking chewing, swallowing and tasting abilities of the user.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An implantable device for inducing salivation by neural stimulation at neurally sensitive locations within an oral or perioral tissue of a user, comprising a housing adapted to be permanently implanted within the oral or perioral tissue, said housing having an enclosure therein, an electrical signal generator disposed in said enclosure, said signal generator including a power source, at least one electrode operatively associated with said housing and electrically coupled to said signal generator, said electrode being so positioned with respect to said housing so as to form an electrical contact with the oral or perioral tissue and in operative contact with a neurally sensitive location of the oral or perioral tissue, the stimulation of which by electrical energy can induce salivation when said housing is operatively disposed, whereby said electrode applies a signal generated by said signal generator to the sensitive location of the oral or perioral tissue to induce salivation.

2. The implantable device of claim 1, further comprising a switch element associated with said housing and said signal generator for activating and deactivating said signal generator.

3. The implantable device of claim 2, wherein said switch element is adapted to protrude from within the oral or perioral tissue into the oral cavity, so as to be operable by the user.

4. The implantable device of claim 2, wherein said switch element includes a potentiometer for controlling a parameter of said signal generated by said signal generator.

5. The implantable device of claim 2, wherein said switch is remote controlled.

6. The implantable device of claim 1, further comprising at least one anchoring element connected to said housing, said at least one anchoring element serves for anchoring the device within the oral or perioral tissue.

7. The implantable device of claim 1, wherein said housing includes a cover.

8. The implantable device of claim 1, wherein said signal generator includes a mechanism for producing a series of pulses having an amplitude of about half to five volts, a pulse width of about 1–1000 micro-seconds and a frequency of about 10–160 Hz.

9. The implantable device of claim 8, wherein said signal generator further includes a mechanism to turn the signal on and off at intervals of about one-half second.

10. A method for stimulating salivation, the method comprising the steps of:

(a) forming at least one cavity in an oral or perioral tissue;

(b) providing at least one implantable device for inducing salivation, including a housing adapted to be permanently implanted within said cavity, said housing having an enclosure therein, an electrical signal generator disposed in said enclosure, said signal generator including a power source, at least one electrode operatively associated with said housing and electrically coupled to said signal generator, said electrode being so positioned with respect to said housing so as to form an electrical contact with the oral or perioral tissue and in operative contact with a neurally sensitive locations of the oral or perioral tissue, the stimulation of which by electrical energy can induce salivation when said housing is operatively disposed, whereby said electrode applies a signal generated by said signal generator to the sensitive locations of the oral or perioral tissue to induce salivation; and (c) implanting said at least one implantable device in said at least one cavity.

11. The method of claim 10, further comprising the steps of locating and stimulating the nerves of the oral or perioral tissue to identify locations which are sensitive to neural stimulation by electrical means prior to forming a cavity in an oral or perioral tissue, wherein said step of forming said cavity in the oral or perioral tissue is effected in said locations.

12. The method of claim 11, wherein said steps of locating and stimulating are performed by applying to the locations an electrical signal of a kind similar to the signal produced by said implantable device.

13. The method of claim 10, wherein said signal generator includes a mechanism for producing a series of pulses having an amplitude of about half to five volts, a pulse width of about 1–1000 micro-seconds and a frequency of about 10–160 Hz.

* * * * *